US008657774B1

(12) United States Patent
Fisher

(10) Patent No.: US 8,657,774 B1
(45) Date of Patent: Feb. 25, 2014

(54) SPINAL DECOMPRESSION DEVICE AND METHOD OF USE

(76) Inventor: Jeff Fisher, Newport Beach, CA (US)

( * ) Notice: Subject to any disclaimer, the term of this patent is extended or adjusted under 35 U.S.C. 154(b) by 68 days.

(21) Appl. No.: 13/572,960

(22) Filed: Aug. 13, 2012

(51) Int. Cl.
*A61F 5/00* (2006.01)

(52) U.S. Cl.
USPC ................................................ 602/32; 602/36

(58) Field of Classification Search
USPC ........................................ 602/32-39; 482/124
See application file for complete search history.

(56) References Cited

U.S. PATENT DOCUMENTS

| | | | | |
|---|---|---|---|---|
| 2,701,564 | A | 2/1955 | Wilhelm | |
| 3,105,489 | A | 10/1963 | Zivi | |
| 3,108,587 | A | 10/1963 | Das | |
| 3,221,735 | A | 12/1965 | Goodman et al. | |
| 4,407,274 | A | 10/1983 | Goodley | |
| 4,865,022 | A | 9/1989 | Gorsen | |
| 4,869,240 | A | 9/1989 | Boren | |
| 4,971,043 | A | 11/1990 | Jones | |
| 5,957,876 | A | 9/1999 | D'Amico | |
| 6,113,564 | A | 9/2000 | McGuire | |
| 6,190,345 | B1 | 2/2001 | Henderson | |
| 6,530,893 | B1 | 3/2003 | Castelli | |
| 7,033,333 | B1 | 4/2006 | Croft et al. | |
| 7,144,380 | B2 | 12/2006 | Gilliam | |
| 7,862,526 | B1 | 1/2011 | Skowron et al. | |
| 2005/0043154 | A1* | 2/2005 | Atrizadeh | 482/124 |
| 2012/0040808 | A1* | 2/2012 | Khademi | 482/124 |

* cited by examiner

*Primary Examiner* — Michael A. Brown
(74) *Attorney, Agent, or Firm* — Stetina Brunda Garred & Brucker

(57) ABSTRACT

There is provided a device for use with a patient. The device includes a first load line including an anchor attachment end and a first inline end. The anchor attachment end is sized and configured to be attachable in a terminating manner to an anchor object. The device further includes a second load line including a head attachment end and a second inline end. The head attachment end is sized and configured to attach to a head of the patient. The device further includes an elastomeric member disposed between and attached to the first and second inline ends. The elastomeric member has a significantly lower linear elastic modulus than each of the first and second load lines. The device further includes an adjustment element sized and configured to adjust the tension in an effective tension length of the device.

20 Claims, 2 Drawing Sheets

SPINAL DECOMPRESSION DEVICE AND METHOD OF USE

CROSS-REFERENCE TO RELATED APPLICATIONS

Not Applicable.

STATEMENT RE: FEDERALLY SPONSORED RESEARCH/DEVELOPMENT

Not Applicable

BACKGROUND

1. Technical Field

The present disclosure generally relates to spinal decompression devices, and more particularly, to a spinal device including an elastomeric element.

2. Related Art

Spinal decompression therapy is a non-surgical, non-invasive treatment for certain types of chronic back pain that works by slowly and gently stretching the spine, taking pressure off compressed discs and vertebrae. A myriad of devices have been developed for providing decompression or applying traction to the human spine. Most of such devices, however, are complex, cumbersome, not readily portable, or require trained healthcare personnel to place the device on the patient and administer treatment. Moreover, some devices require the patient to actively apply a force or counter-force with the hands, legs or feet. This is counter to the decompression goals of getting the muscles of the patient to relax and lengthen. Accordingly, there is a need in the art for an improved ease to use spinal decompression device.

BRIEF SUMMARY

According to an aspect of the invention, there is provided a spinal decompression device for use with a patient and an anchor object. The device includes a first load line including an anchor attachment end and a first inline end. The anchor attachment end is sized and configured to be attachable in a terminating manner to the anchor object. The device further includes a second load line including a head attachment end and a second inline end. The head attachment end is sized and configured to attach to a head of the patient. The device further includes an elastomeric member disposed between and attached to the first and second inline ends. The elastomeric member has a significantly lower linear elastic modulus than each of the first and second load lines. The device further includes an effective tension length segment of the device being collectively defined by those portions of the first load line, the elastomeric member and the second load line that are in tension when opposing forces are applied to the anchor attachment end and the head attachment end to place the first load line, the elastomeric member and the second load line in tension. The device further includes an adjustment element in communication with the effective tension length segment sized and configured to adjust the tension in the effective tension length segment.

According to various embodiments, the anchor attachment end may include a loop segment. The first and second load lines may be formed of a flexible elongate material. The first and second load lines may be formed of a strap material, which may be formed of a nylon material for example. The elastomeric member may include a first fixture attached to the first load line, and a second fixture attached to the second load line, and an elastomeric element disposed between and attached to the first and second fixtures. The elastomeric element may be in the form of elastomeric tubing. The elastomeric tubing may be formed of a rubberized material. The elastomeric element may include multiple portions disposed between and attached to the first and second fixtures. The adjustment element may be sized and configured to adjust the tension in the effective tension length segment by changing the length of the first or second load lines. The adjustment element may include a buckle.

In addition, the first load line may include a first segment and a second segment. The first segment may extend from the elastomeric member to the buckle and the second segment may extend from the buckle. The first segment is in tension with the effective tension length segment being in tension. The first and second segments are a continuous piece of material. The first and second segments and the buckle are sized and configured to reduce a length of the first segment upon a pulling of the second segment in a direction away from the buckle. Further, the adjustment element may be sized and configured to adjust the tension in the effective tension length segment by applying a force along the first or second load lines in a direction towards the head attachment end. The device may include release line attached to the second load line.

According to another embodiment, there is provided a method of decompression of a spine of a patient. The method includes providing a cervical spine decompression device. The device includes a first load line including an anchor attachment end and a first inline end. The device further includes a second load line including a head attachment end and a second inline end. The device further includes an elastomeric member disposed between and attached to the first and second inline ends. The elastomeric member has a significantly lower linear elastic modulus than each of the first and second load lines. The device further includes an effective tension length segment of the device being collectively defined by those portions of the first load line, the elastomeric member and the second load line that are in tension when opposing forces are applied to the anchor attachment end and the head attachment end to place the first load line, the elastomeric member and the second load line in tension. The method further includes attaching the head attachment end to a head of the patient. The method further includes attaching the anchor attachment end to an anchor object with the first load line terminated adjacent to the anchor object. The method further includes positioning the patient laying supine face-up to place the device in tension with the elastomeric member stretched in elastic deformation.

According to various embodiments, the anchor object may be a door handle. The method may further include adjusting the tension in the effective tension length segment by changing a length of the first or second load line. In an embodiment, the first load line includes a first segment and a second segment. The first segment extends from the elastomeric member to the buckle and the second segment extends from a buckle. The method may further include pulling upon the second segment in a direction away from the buckle to reduce a length of the first segment and increase a length of the second segment. The adjustment element may be sized and configured to adjust the tension in the effective tension length segment by applaying a force along the first or second load lines in a direction towards the head attachment end. There may be provided a release line that is attached to the second load line, and the method may include pulling upon the release line in a direction toward the head attachment end to decrease the tension in the second load line at the head attachment end.

The presently contemplated embodiments will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently preferred embodiments of the invention, and is not intended to represent the only form in which the present devices may be developed or utilized. It is to be understood, however, that the same or equivalent functions may be accomplished by different embodiments that are also intended to be encompassed within the spirit and scope of the invention. It is further understood that the use of relational terms such as first, second, and the like are used solely to distinguish one from another entity without necessarily requiring or implying any actual such relationship or order between such entities.

Figure 1:
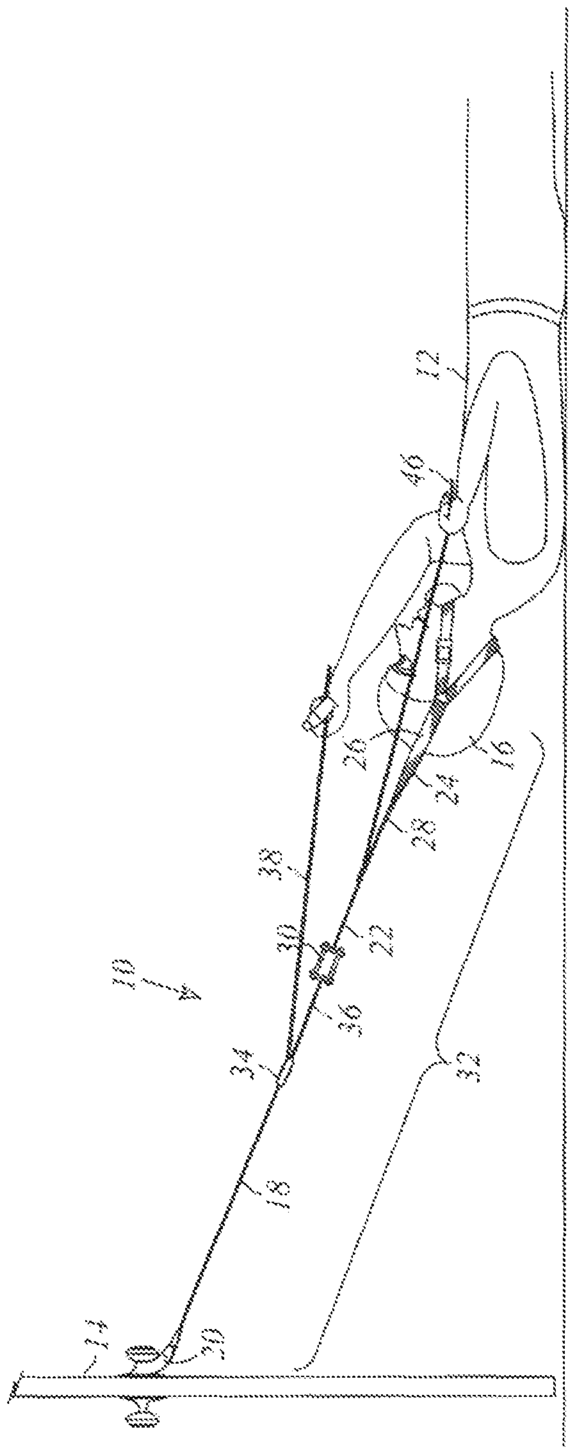
FIG. 1 depicts a perspective view of a spinal decompression device as being used by a patient and attached to an anchor object according to an aspect of the invention.
Figure 2:
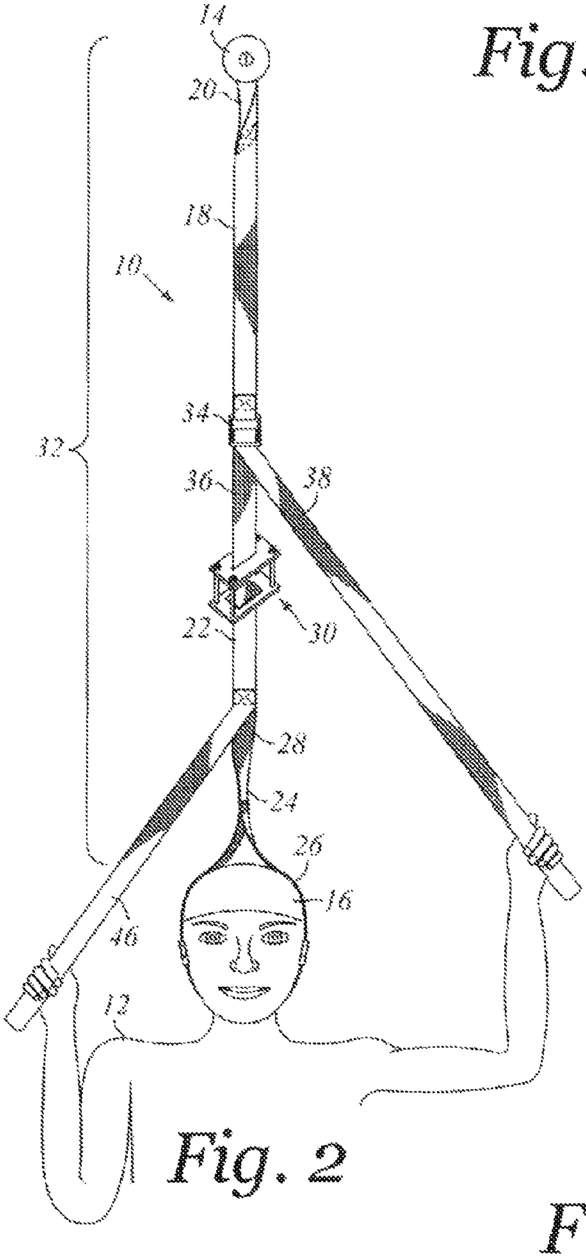
FIG. 2 depicts a top view of the patient and the decompression device of FIG. 1.

Referring now FIG. 1 there is depicted a perspective view of a perspective view of a spinal decompressing device 10 as being used by a patient 12 and attached to an anchor object 14 according to an aspect of the invention. FIG. 2 depicts a top view of the patient and the decompression device 10 of FIG. 1. As is illustrated, the patient 12 is laying supine upon a floor. The decompression device 10 is attached to the head 16 of the patient 12.

According to an aspect of the invention, there is provided the cervical spine decompression device 10 for use with the patient 12 and the anchor object 14. The device 10 includes a first load line 18 including an anchor attachment end 20 and a first inline end 22. The anchor attachment end 20 is sized and configured to be attachable in a terminating manner to the anchor object 14. The device 10 further includes a second load line 24 including a head attachment end 26 and a second inline end 28. The head attachment end 26 is sized and configured to attach to the head 16 of the patient 12. The device 10 further includes an elastomeric member 30 disposed between and attached to the first and second inline ends 22, 28. The elastomeric member 30 has a significantly lower linear elastic modulus than each of the first and second load lines 18, 24. The device 10 further includes an effective tension length segment 32 of the device 10 being collectively defined by those portions of the first load line 18, the elastomeric member 30 and the second load line 24 that are in tension when opposing forces are applied to the anchor attachment end 20 and the head attachment end 26 to place the first load line 18, the elastomeric member 30 and the second load line 24 in tension. The device 10 further includes an adjustment element 34 in communication with the effective tension length segment 32 sized and configured to adjust the tension in the effective tension length segment 32.

According to various embodiments, the first and second load lines 18, 24 may be formed of a flexible elongate material. The first and second load lines 18, 24 may be formed of any of those materials which are well known to one of ordinary skill in the art, such as a strap material of a nylon material or nylon mesh material. Other materials, such as ropes, cords and the like may be used as well.

The anchor attachment end 20 may include a loop segment. The loop segment may be easily secured to the anchor object 14, such as a door knob or handle as is illustrated in the depicted embodiment. Where the first load line 18 is formed of a strap material, the loop segment may be readily formed by stitching the end of the first load line 18 back upon itself. The loop segment may be attached to the anchor object 14 by being looped about it.

As mentioned above, the anchor attachment end 20 is sized and configured to be attachable in a terminating manner to the anchor object 14. As used herein "terminating manner" refers to the first load line 18 being attached at the anchor attachment end 20 in a manner that does not modify the effective tension length segment 32 during use of the decompression device 10. Thus, the attachment end 20 is not attached at the anchor object 14 with any sort of pulley or pivot or deflection point. Rather the anchor attachment end 20 is intended to be fixed with respect to the anchor object 14 during use of the decompression device 10.

The head attachment end 26 may include any form of loop or harness arrangement. May be sized and configured to be looped about a base of a patient's head. A chin strap may also be used. The head attachment end 26 may have removable fasteners, such as plastic side-release type of inline connectors as is commonly used with nylon strap material, may be used to facilitate an ease of attachment to the patient's head. With this general configuration, the decompression device 10 may be attached to the anchor object 14 with the anchor attachment end 20 and to the head 16 of the patient 12 with the head attachment end 26. The patient 12 may lay supine with the decompression device 10 disposed in tension along the effective tension length segment 32. Such tension results in a pulling force applied to the head 16 of the patient 12. This pulling force is used for decompression of the spine of the patient 12.

The elastomeric member 30 may include a first fixture 40 attached to the first load line 18, and a second fixture 42 attached to the second load line 24. An elastomeric element is disposed between and attached to the first and second fixtures 40, 42. The elastomeric element may be in the form of elastomeric tubing 44 (individual segments denoted as 44*a-d*). The elastomeric element may include multiple portions (such as the elastomeric tubing 44*a-d*) disposed between and attached to the first and second fixtures 40, 42. The elastomeric tubing 44 may be formed of a rubberized material, such as a silicon rubber. The particular material selection and configuration for the elastomeric member 30 may be chosen from those which are well known to one of ordinary skill in the art. The first and second fixtures 40, 42 may take the form of simple plate like elements of various shapes and may made as plastic. The elastomeric tubing 44*a-d* may be easily attached to the first and second fixtures 40, 42 by being inserted through holes formed in the formed in the first and second fixtures 40, 42 and knots formed in the ends of the elastomeric tubing 44*a-d*. In addition, the elastomeric member 30 may be readily attached to the first and second inline ends 22, 28 through the use of a slot formed in each of the first and second fixtures 40. 42. The first and second inline ends 22, 28 may be sewn to terminate in a T-shaped configuration. Installation of the first and second inline ends 22, 28 would include folding to top of the T-shape back upon the first and second includes ends 22, 28 and inserting the same through the slots. Thereafter the top of the T-shape may be unfolded, thereby mitigating unwanted detachment. Other ways of attaching the first and second inline ends 22, 28 may be implemented which are well known to one of ordinary skill in the art.

Figure 3A:
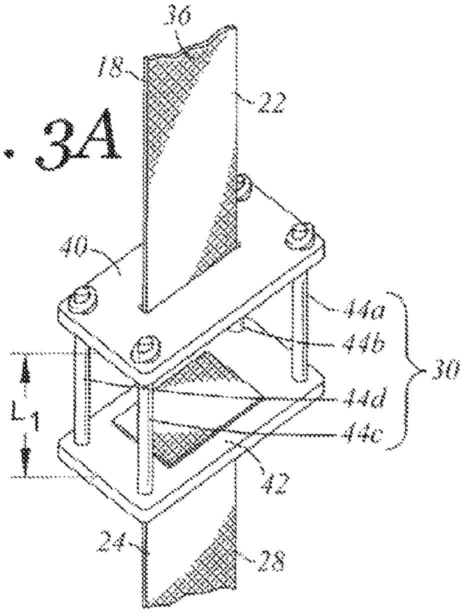
FIG. 3A is an enlarged perspective view of an elastomeric member of the decompression device of FIG. 1.
Figure 3B:
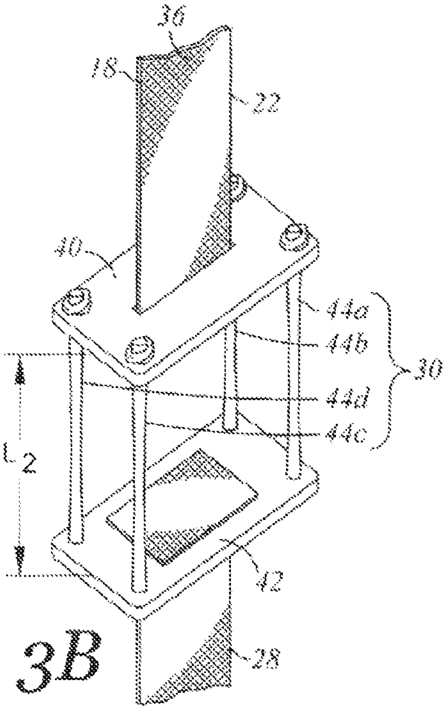
FIG. 3B is an enlarged perspective view of the elastomeric member of FIG. 3A with the elastomeric member disposed in tension.

Referring now to FIGS. 3A and 3B, there is illustrated an enlarged perspective view of a portion of the decompression device 10 that includes the elastomeric member 30 in the form of the tubing 44*a-d*. The linear length L1 indicates that length of the tubing 44*a-d* while the tubing 44*a-d* is at its natural length (neither in tension or compression). The linear length L2 indicates that length of the tubing 44*a-d* while the tubing 44*a-d* is disposed in tension, such as when the decompression device 10 in use.

As mentioned above, the elastomeric member 30 has a significantly lower linear elastic modulus than each of the first and second load lines 18, 24. In the embodiment illustrated, it is contemplated that the linear elastic modulus of the elastomeric member 30 that includes the tubing 44*a-d* in the form of silicon rubber tubing is significantly lower than the linear elastic modulus of the first and second load lines 18, 24 in the form of nylon mesh strap material. In this regard, for a given amount of tension in the effective tension length segment 32, the elastomeric member 30 is configured to linearly elongate much more than the first and second load lines 18, 24.

This difference in the linear elastic modulus is particularly effective in the use of the decompression device 10 to maintain a relatively constant force to the patient's head 16 during use. During use of the decompression device 10, it is anticipated that the patient's muscles and soft tissue about the patient's vertebrae would tend to "relax" or otherwise allow for the lengthening of the patent's spine. This in turn would result in a slight movement of the head 16 of the patient 10 towards the second load line 24. However, the use of the elastomeric member 30 (with the tubing 44*a-d* stretched) allows the decompression device 10 to accommodate for such slight movement. This mitigates against the potential slackening of the first and second load lines 18, 24 that may result in a lessening of tension therein. The stretched elastomeric member 30 may decrease in length as a result of the movement of the head 16 of the patient 12 while still being stretched or otherwise elongated. This maintains a continuity of tension in the second load line 24, and therefore a continuity of force being applied to the patient 12.

The adjustment element 34 may be sized and configured to adjust the tension in the effective tension length segment 32 by changing the length of the first or second load lines 18, 24. In this regard, the adjustment element 34 may be sized and configured to increase the tension in the effective tension length segment 32. For example, the adjustment element 34 may include a buckle. In addition, the first load line may include a first segment 36 and a second segment 38. The first segment 36 may extend from the elastomeric member 30 to the buckle and the second segment 38 may extend from the buckle. The first segment 36 is in tension with the effective tension length segment 32 being in tension. The first and second segments 36, 38 may be a continuous piece of material. The first and second segments 36, 38 and the buckle are sized and configured to reduce a length of the first segment 36 upon a pulling of the second segment 38 in a direction away from the buckle. Other arrangements for adjusting the tension length segment 32 may be implemented such as those that utilize a ratchet, straps adjusters, double rings, and the like.

The adjustment element may be sized and configured to adjust the tension in the effective tension length segment 32 by applying a force along the first or second load lines 18, 24 in a direction towards the head attachment end 26. For example, in the embodiment depicted, the adjustment element includes a release line 46 attached to the second load line 24 at a connection location 48. A pulling motion upon the release line 46 with a force component in a direction along the second load line 24 in a direction towards the head attachment end 26 away from or opposite the anchor attachment end 20 while the first and second load lines 18, 24 are in tension results in the a reduction of the tension in the effective tension length segment 32 (the effective tension length segment 32 being modified to that portion of the second load line 24 between the connection location 48 and the head attachment end 26 that is disposed in tension). It is contemplated that the use of the adjustment element, such release line 46, provides the patient 12 with a simple readily actuated solution to immediately reduce tension in the second load line 24 while using the decompression device 10 in the supine position. This is especially beneficial in instances where the patient experiences pain or discomfort while using the decompression device 10. The use of the release line 48 as an adjustment member is also advantageous with respect to manufacturability and cost.

According to another embodiment, there is provided a method of decompression of a spine of the patient 12. The method includes providing the cervical spine decompression device 10. The device 10 includes the first load line 18 including the anchor attachment end 20 and the first inline end 22. The device 10 further includes the second load line 24 including the head attachment end 26 and the second inline end 28. The device 10 further includes the elastomeric member 30 disposed between and attached to the first and second inline ends 22, 28. The elastomeric member 30 has a significantly lower linear elastic modulus than each of the first and second load lines 18, 24. The device 10 further includes the effective tension length segment 32 of the device 10 being collectively defined by those portions of the first load line 18, the elastomeric member 30 and the second load line 24 that are in tension when opposing forces are applied to the anchor attachment end 20 and the head attachment end 26 to place the first load line 18, the elastomeric member 30 and the second load line 24 in tension. The method further includes attaching the head attachment end 26 to the head 16 of the patient 12. The method further includes attaching the anchor attachment end 20 to the anchor object 14 with the first load line 18 terminated adjacent to the anchor object 14. The method further includes positioning the patient 12 laying supine to place the device 10 in tension with the elastomeric member 30 stretched in elastic deformation.

The difference in the linear elastic modulus is particularly effective in the use of the decompression device 10 to maintain a relatively constant force to the patient's head 16 during use. This mitigates against the potential slackening of the first and second load lines 18, 24 that may result in a lessening of tension therein. The stretched elastomeric member 30 may decrease in length as a result of movement of the head 16 of the patient 12 while still being stretched or otherwise elongated. This maintains a continuity of tension in the second load line 24, and therefore a continuity of force being applied to the patient 12.

It is contemplated that the angle between the decompression device 10 and the horizontal plane (the floor upon which the patient is laying face up) may preferably be between 5 and 30 degrees. This results not only in a force directly in line with the spine, but also a force component slightly forward. This places the neck in flexion (tilting forward). In certain cases, such forward force may be beneficial is to the decompression goals of the patient 12. As such a suitable readily available anchor object 14 is a door knob or handle. The angle may be easily adjusted as desired by selecting an appropriate horizontal distance between the head of the patient 10 and the anchor object 14, as well as making length adjustments to the various segments of the decompression device 10. The angle may also be adjusted by attaching the device 10 at other heights. For example the closure of a door and the door jam may be used to secure the anchor attachment end 20 at any range of heights. The bottom of a door may also be a convenient location to secure the device 10 where little or no angle with respect to the horizontal plane is desired. It is contemplated that use of a door enables implementation the device 10 in nearly any setting, including for home use.

According to various embodiments, the method may further include adjusting the tension in the effective tension length segment 32 by changing a length of the first or second load line 18, 24. In an embodiment, the first load line includes a first segment and a second segment. The first segment extends from the elastomeric member 30 to the adjustment member 34 in the form of a buckle and the second segment 38 extends from a buckle. The method may further include pulling upon the second segment 38 in a direction away from the buckle to reduce a length of the first segment 36 and increase a length of the second segment 38. In this regard, the patient 12 may readily tighten the device 10 by simply pulling upon the second segment 38. As the spine of the patient undergoes a lengthening during decompression, the tension in the effective length segment 30 may be maintained by reducing the length of the first segment 36.

The adjustment element 34 may be sized and configured to adjust the tension in the effective tension length segment 30 by applying a force along the first or second load lines 18, 24 in a direction towards the head attachment end 26. There may be provided a release line 26 that is attached to the second load line 24, and the method may include pulling upon the release line 26 in a direction toward the head attachment end 26 to decrease the tension in the second load line 24 at the head attachment end 26. It is contemplated that the use of the adjustment element 32, such release line 46, provides the patient 12 with a simple readily actuated solution to immediately reduce tension in the second load line 24 while using the decompression device 10 in the supine position.

The particulars shown herein are by way of example and for purposes of illustrative discussion of the embodiments of the present invention only and are presented in the cause of providing what is believed to be the most useful and readily understood description of the principles and conceptual aspects. In this regard, no attempt is made to show more details than is necessary for a fundamental understanding of the disclosure, the description taken with the drawings making apparent to those skilled in the art how the several forms of the presently disclosed invention may be embodied in practice.

What is claimed is:

1. A spinal decompression device for use with a patient and an anchor object, the device comprising:
- a first load line including an anchor attachment end and a first inline end, the anchor attachment end being sized and configured to be attachable in a terminating manner to the anchor object;
- a second load line including a head attachment end and a second inline end, the head attachment end being sized and configured to attach to a head of the patient;
- an elastomeric member disposed between and attached to the first and second inline ends, the elastomeric member having a significantly lower linear elastic modulus than each of the first and second load lines;
- an effective tension length segment of the device being collectively defined by those portions of the first load line, the elastomeric member and the second load line that are in tension when opposing forces are applied to the anchor attachment end and the head attachment end to place the first load line, the elastomeric member and the second load line in tension; and
- an adjustment element in communication with the effective tension length segment sized and configured to adjust the tension in the effective tension length segment.

2. The device of claim 1 wherein the anchor attachment end includes a loop segment.

3. The device of claim 1 wherein the first and second load lines are formed of a flexible elongate material.

4. The device of claim 1 wherein the first and second load lines are formed of a strap material.

5. The device of claim 4 wherein the first and second load lines are formed of a nylon material.

6. The device of claim 1 wherein the elastomeric member includes a first fixture attached to the first load line, and a second fixture attached to the second load line, and an elastomeric element disposed between and attached to the first and second fixtures.

7. The device of claim 6 wherein the elastomeric element is in the form of elastomeric tubing.

8. The device of claim 7 wherein the elastomeric tubing is formed of a rubberized material.

9. The device of claim 6 wherein the elastomeric element includes multiple portions disposed between and attached to the first and second fixtures.

10. The device of claim 1 wherein the adjustment element is sized and configured to adjust the tension in the effective tension length segment by changing the length of the first or second load lines.

11. The device of claim 1 wherein the adjustment element includes a buckle.

12. The device of claim 11 wherein the first load line includes a first segment and a second segment, the first segment extends from the elastomeric member to the buckle and the second segment extends from the buckle, the first segment is in tension with the effective tension length segment being in tension, the first and second segments are a continuous piece of material, the first and second segments and the buckle are sized and configured to reduce a length of the first segment upon a pulling of the second segment in a direction away from the buckle.

13. The device of claim 1 wherein the adjustment element is sized and configured to adjust the tension in the effective tension length segment by applaying a force along the first or second load lines in a direction towards the head attachment end.

14. The device of claim 1 further includes a release line attached to the second load line.

15. A method of decompression of a spine of a patient, the method comprising:
- a) providing a cervical spine decompression device including:
  - a first load line including an anchor attachment end and a first inline end;
  - a second load line including a head attachment end and a second inline end;
  - an elastomeric member disposed between and attached to the first and second inline ends, the elastomeric member having a significantly lower linear elastic modulus than each of the first and second load lines; and an effective tension length segment of the device being collectively defined by those portions of the first load line, the elastomeric member and the second load line that are in tension when opposing forces are applied to the anchor attachment end and the head attachment end to place the first load line, the elastomeric member and the second load line in tension;

b) attaching the head attachment end to a head of the patient;

c) attaching the anchor attachment end to an anchor object with the first load line terminated adjacent to the anchor object;

d) positioning the patient laying supine to place the device in tension with the elastomeric member stretched in elastic deformation.

16. The method of claim 15 wherein the anchor object is a door handle.

17. The method of claim 15 further includes adjusting the tension in the effective tension length segment by changing a length of the first or second load lines.

18. The method of claim 15 wherein the first load line includes a first segment and a second segment, the first segment extends from the elastomeric member to the buckle and the second segment extends from a buckle, step e) includes pulling upon the second segment in a direction away from the buckle to reduce a length of the first segment and increase a length of the second segment.

19. The method of claim 15 further includes adjusting the tension in the effective tension length segment by applying a force along the first or second load lines in a direction towards the head attachment end.

20. The method of claim 19 wherein the a release line is attached to the second load line, step e) includes pulling upon the release line in a direction toward the head attachment end to decrease the tension in the second load line at the head attachment end.

* * * * *